United States Patent
Richard

(10) Patent No.: US 6,942,485 B1
(45) Date of Patent: Sep. 13, 2005

(54) DENTAL HANDPIECE COMPRISING TORQUE-LIMITING MEANS

(75) Inventor: Hervé Richard, Notre Dame de Bellecombe (FR)

(73) Assignee: Anthogyr, Sallanches (FR)

( * ) Notice: Subject to any disclaimer, the term of this patent is extended or adjusted under 35 U.S.C. 154(b) by 281 days.

(21) Appl. No.: 10/088,710

(22) PCT Filed: Oct. 2, 2000

(86) PCT No.: PCT/FR00/02723

§ 371 (c)(1),
(2), (4) Date: Mar. 20, 2002

(87) PCT Pub. No.: WO01/22898

PCT Pub. Date: Apr. 5, 2001

(30) Foreign Application Priority Data

Sep. 30, 1999 (FR) .................................. 99 12376

(51) Int. Cl.[7] ............................................... A61C 1/07
(52) U.S. Cl. .................................................... 433/118
(58) Field of Search ....................... 433/126, 114, 118, 433/122, 123, 124, 125, 128, 127; 81/478, 81/476, 474; 464/35, 36, 139

(56) References Cited

U.S. PATENT DOCUMENTS

| | | | | |
|---|---|---|---|---|
| 2,514,227 A | * | 7/1950 | Dodge ..................... | 192/104 C |
| 3,727,432 A | * | 4/1973 | Eaves et al. ................... | 464/35 |
| 3,827,260 A | * | 8/1974 | Kato ............................. | 464/35 |
| 3,852,884 A | | 12/1974 | Lazarus .......................... | 32/63 |
| 4,617,837 A | * | 10/1986 | Kataoka et al. ............. | 475/189 |
| 4,861,201 A | * | 8/1989 | Cuilleron ..................... | 408/139 |
| 5,584,689 A | | 12/1996 | Loge ............................ | 433/128 |
| 5,924,864 A | | 7/1999 | Logé et al. .................. | 433/118 |
| 6,176,703 B1 | * | 1/2001 | Gugel et al. ................. | 433/120 |

FOREIGN PATENT DOCUMENTS

DE          27 26 325 A     12/1978

* cited by examiner

Primary Examiner—Melba Bumgarner
(74) Attorney, Agent, or Firm—RatnerPrestia

(57) ABSTRACT

A dental handpiece is provided including a neck wherein balls are guided in transverse channels of an input shaft and are radially spaced apart by a support piece including a tapered part thrust by a spring. A linking ring is mounted on the end of the input shaft and includes internal longitudinal grooves circular in cross-section and of variable depth along the longitudinal direction. The linking ring is mounted sliding and locked in rotation on an output shaft. Under the action of a resisting torque applied by the tool to the output shaft greater than a predetermined threshold, the linking balls are subjected to a reaction from the internal grooves of the linking ring which tends to bring them closer together, countering the spring. The balls are then released, producing a disengagement which limits the transmitted torque and prevents the tool engaged in the tool-bearing shaft from breaking.

21 Claims, 5 Drawing Sheets

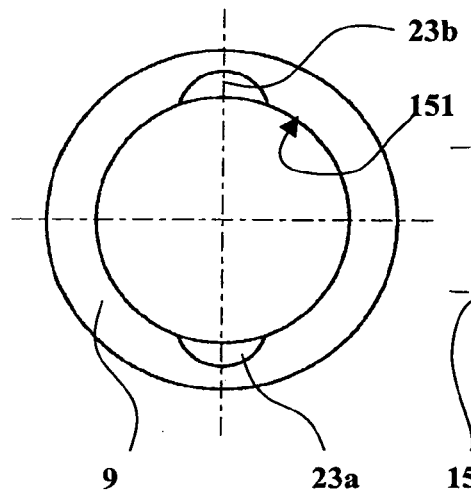
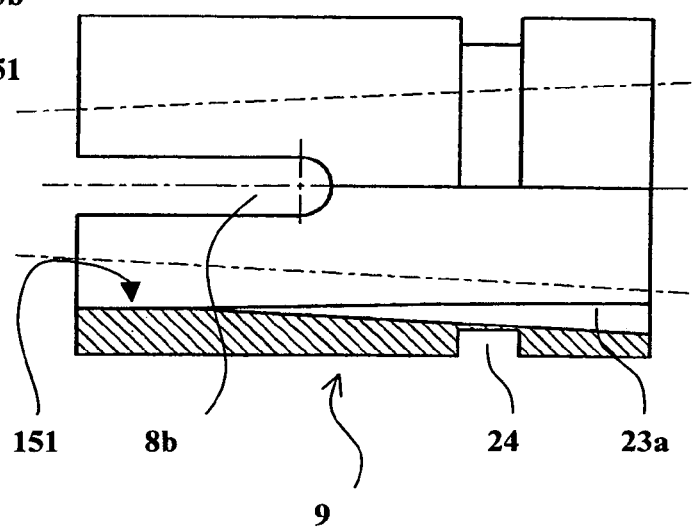
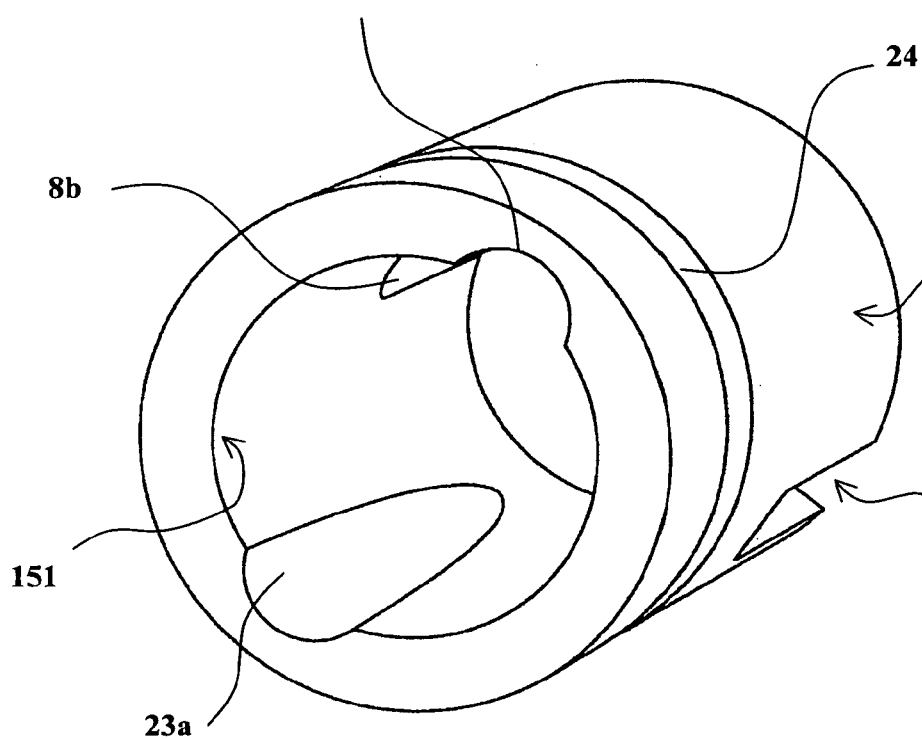

DENTAL HANDPIECE COMPRISING TORQUE-LIMITING MEANS

This application is the U.S. national phase application of PCT International Application No. PCT/FR00/02723 filed 2 Oct. 2000.

TECHNICAL FIELD OF THE INVENTION

The present invention concerns handpieces, used in dentistry, on which a rotary dental tool can be mounted and driven in unidirectional rotation about its axis.

Small rotary tools are often used to work in the mouth, for example rasps for working on root canals, which take the form of a fine rod holded oblique or perpendicular to the general direction of entry into the mouth. A swan-neck dental handpiece is generally used for this purpose, which the dentist can couple mechanically to an electric or pneumatic motor. Swan-neck dental handpieces have a main body coaxial with the rotation axis of the drive motor and in which there is a longitudinal bore, followed by a portion called the neck at an angle of the order of 15° to 30° to the body and in which there is also a longitudinal bore, and finally a portion called the head that is perpendicular or substantially perpendicular to the neck and includes a transverse bore that communicates with the longitudinal bore in the neck. This head includes a tool-holder for separably fixing a tool.

A transverse tool-carrier shaft is mounted to rotate about a transverse axis in the transverse bore, and includes a tool-holder for separably fixing a tool to the tool-carrier shaft. A drive shaft is mounted in the longitudinal bore to rotate about a longitudinal axis. A pair of pinion gears mounted at the end of the drive shaft and meshing with a ring gear mounted on the tool-carrier shaft transmits torque between the drive shaft and the tool-carrier shaft. The other end of the drive shaft is provided with coupling means for driving it in rotation by means of a motor, which is generally interchangeable. The motor generally rotates at high speed and is associated with a speed reducer for transmitting an appropriate lower speed, depending on the tool.

This type of dental handpieces is at present frequently used with flexible rasps, made of nickel and titanium alloy, for example, which must be driven in unidirectional rotation at relatively slow speeds of the order of 300 rpm, and which have the advantage of being sufficiently flexible to follow the often curved longitudinal profile of root canals.

It sometimes happens that the tool digs into or becomes wedged in the root canal. There is then the risk of damage to the root canal and, more importantly, of breaking the rasp. Obviously, removing a broken section of rasp wedged into the very narrow root canal is a difficult operation. It is often impossible to remove this broken section and therefore impossible to complete the treatment of the root canal.

To prevent or reduce the risk of tools breaking if they dig into the material of the tooth, it has been proposed to use an electric drive motor provided with a torque limiter. A solution of this kind is costly, on the one hand because the torque limiter is itself costly and on the other hand because it cannot be fitted to existing motors that the dentist has already acquired.

The document DE 27 26 325 proposes to fit a clutch between the output of the drive motor and the flexible cable for transmitting the motion to the handpiece; the driving shaft has a prism-shaped outside surface against which bear coupling balls that can move in radial channels of the driven shaft. The maximum torque transmitted cannot be adjusted, which makes the handpiece unsuitable for use in endodontal work, because it is usually necessary to employ several tools in succession having different diameters and therefore different permissible maximum torques. Also, the clutch is far away from the tool and the handpiece itself is subject to a wide spread in terms of the permissible maximum torque transmitted to the tool.

The document U.S. Pat. No. 5,924,864 proposes incorporating an adjustable clutch into the body of the handpiece. The clutch includes two radial plates bearing frontally on each other; a first plate is fastened to the driving shaft, a second plate is fastened to the driven shaft, and the plates are spring-loaded by an axial compression spring whose force can be adjusted by axial movement of a peripheral adjuster ring. The plates have irregular surfaces on their contact faces that rub against each other. This results in progressive wear of the plates in service. The plates have a relatively large diameter, which prevents them from being located in the neck of the handpiece, which is necessarily narrow so that it can be inserted into the mouth. It is therefore necessary to locate the clutch in the body of the handpiece, away from the tool. Adjusting the maximum torque that can be transmitted by maneuvering the peripheral ring requires dentists to use their other hand, their first hand being placed on the neck of the handpiece to hold the handpiece in the mouth. Also, the clutch is separated from the tool by a mechanical transmission with two successive changes of angle, which affects the precision with which the limit maximum torque that can be transmitted can be adjusted.

SUMMARY OF THE INVENTION

The problem addressed by the present invention is that of automatically limiting the drive torque of a rotary dental tool by different, simple and inexpensive mechanical means incorporated into the handpiece itself without increasing its overall volume, so that dentists can use all types of motors and in particular motors they already have that have no torque limiter.

The invention preferably also aims to ensure satisfactory precision and reproducibility of the maximum limit torque transmitted by the handpiece to the tool so that the maximum limit torque can be matched to the tool to be used and the tool used most efficiently, i.e. at slightly below the permissible maximum limit torque before it breaks.

In practice the order of magnitude of the limit maximum torque depends on the tool, and for the flexible rasps used at present, this maximum torque is from approximately 0.3 N.cm to approximately 5 N.cm.

Another object of the invention is to ensure efficient operation of the tool, and therefore regular and efficient positive driving of the tool by the handpiece as long as the limit maximum torque is not reached.

The aim is to provide the above functions with the smallest possible number of component parts, in order to reduce the cost of fabrication and assembly.

In accordance with the invention, the limit maximum torque transmitted by the handpiece to the tool must be adjustable at will, so that the dentist using the handpiece can match the limit maximum torque to different tools that may be used successively in the same handpiece, for example during the same endodontic treatment. In this way, the handpiece operates the various tools under their best conditions of use.

The adjustment means must preferably be directly accessible to the hand of the dentist holding the handpiece, without requiring use of the other hand or interfering with the holding or positioning of the handpiece.

In accordance with the invention, the tool drive torque is preferably limited not only in the forward direction of working of the tool, for removing dental material, but also in the reverse direction, for example to extract the tool from a root canal. The two permissible maximum torque limits can then be different, depending on the rotation direction. A higher limit torque is acceptable for the reverse rotation direction, for extracting the tool, and a lower limit torque in the forward rotation direction, for working with the tool.

To achieve the above and other objects, the invention provides a dental handpiece for driving continuous rotation of a dental tool, said handpiece including a drive shaft mounted to rotate in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted; the torque limiter means include:
  a male coupling portion constrained to rotate with the first shaft of the pair of shafts comprising the primary shaft and secondary shaft, and having a coaxial annular outside surface,
  a female coupling portion constrained to rotate with the second shaft of the pair of shafts comprising the primary shaft and the secondary shaft, and having a coaxial annular inside surface overlapping the coaxial annular outside surface of the male coupling portion,
  a series of coupling cavities distributed annularly over the coaxial annular surface of the first coupling portion of the pair of coupling portions comprising the male and female coupling portions,
  at least one rotary coupling member with a parallel rotation axis, mounted to slide radially in a transverse passage of the second coupling portion of the pair of coupling portions comprising the male and female coupling portions, and spring-loaded by spring means toward the coaxial annular surface of the first coupling portion of the pair of coupling portions comprising the male and female coupling portions so as to be partially engaged in said coupling cavities whilst remaining guided in said transverse passage.

The dental handpiece according to the invention preferably includes at least two rotary coupling members mounted to slide radially in respective transverse passages regularly distributed around the longitudinal axis to balance the radial forces of the rotary coupling members between the male and female coupling portions.

The connecting rotary members can be cylindrical rollers, barrel-shaped rollers, or, more simply and advantageously, connecting balls.

Obviously the connecting rotary members can be housed in respective transverse passages either of the female connecting portion or of the male connecting portion. It may nevertheless be advantageous, in particular in order to reduce the overall size and to facilitate adjustments, for the rotary coupling member(s) to be mounted to slide radially in a respective transverse passage in the male coupling portion and the coupling cavities to be distributed annularly over the coaxial annular surface of the female coupling portion.

One embodiment of the dental handpiece includes means for adjusting the force of the spring means spring-loading the rotary coupling member(s). A first option is for the adjuster means to constitute the means for adjusting the maximum torque that can be transmitted by the torque limiter means.

It is more advantageous if the means for adjusting the force of the spring means merely constitute calibration means that are factory set and not accessible to the dentist, and different means are provided for intentional adjustment of the permissible maximum torque by the dentist. To provide said other means for adjusting the maximum torque that can be transmitted, a dental handpiece can advantageously be provided in which:
  the coupling cavities are longitudinal grooves with a circular arc-shaped cross section and a depth varying in the longitudinal direction,
  relative longitudinal position adjustment means accessible to the user are provided for adjusting the relative longitudinal position of the male coupling portion in the female coupling portion,
  so that the rotary coupling member(s) engage(s) in deeper or shallower portions of the coupling cavities as a function of the chosen relative longitudinal position, which determines the maximum torque that can be transmitted.

A first option is for the transverse channel(s) to be oriented in radial directions. In this case the maximum torque that can be transmitted is the same in both rotation directions.

The transverse passage(s) are/is preferably oriented obliquely to the radial directions. In this case, the maximum torques that can be transmitted differ according to the rotation direction.

In one practical embodiment, in a dental handpiece according to the invention:
  the male coupling portion is the distal end of the primary shaft,
  the female coupling portion is a coupling ring mounted to overlap the adjacent ends of the primary shaft and the secondary shaft, and coupled to the secondary shaft by rotation-preventing means,
  the distal end of the primary shaft includes transverse passages for guiding coupling balls,
  the distal end of the primary shaft includes an axial bore into which the transverse passages open,
  a bearing portion is mounted to slide axially in said axial bore and has a frustoconical part in contact with the coupling balls to urge them radially outward,
  a compression spring is engaged axially between the bearing member and a calibration screw itself functionally engaged in a screwthreaded section of the axial bore.

Obviously, the connecting ring can be constrained to rotate with either the primary shaft or the secondary shaft. It may nevertheless be preferable to constrain the connecting ring to rotate with the secondary shaft. In this case, a dental handpiece is such that:
  the coupling ring is slidably mounted on the proximal end of the secondary shaft, and includes coupling cavities in the form of longitudinal grooves whose depth varies in the longitudinal direction,
  the coupling ring is freely rotatable and is constrained to move in axial translation with an adjuster ring itself slidably mounted on the handpiece body to be directly accessible to the user.

Thanks to its position in the handpiece itself, at the end of the transmission system, the mechanical clutch in accordance with the invention operates on components moving relatively slowly, which are therefore subjected to relatively high torques. The precision and reproducibility of the limit torque or clutch release torque are therefore obtained more easily. Also, frictions and loss of efficiency are minimized in the portion of the transmission system between the clutch and the tool, so that the value of the maximum torque applied to the tool is close to the clutch release torque and is not affected by the downstream mechanical transmission.

In the same line of thinking, to improve further the precision and reproducibility of the limit torque or clutch release torque, a dental handpiece can advantageously be provided that includes a main handpiece body, a handpiece neck and a handpiece head, and the torque-limiter means are housed in the neck of the handpiece itself, i.e. as close as possible to the tool. This is made possible by the small dimensions of the particular means in accordance with the invention of adjusting the maximum torque that can be transmitted.

BRIEF DESCRIPTION OF THE DRAWINGS

Other objects, features and advantages of the present invention will emerge from the following description of particular embodiments, which is given with reference to the accompanying drawings, in which:

FIG. 6 is an outside view, from the right-hand side with reference to FIG. 7, of the sliding coupling ring;

FIG. 7 is a view of the sliding coupling ring, half in section and half in external view;

FIG. 8 is a perspective view of the sliding coupling ring;

DESCRIPTION OF THE PREFERRED EMBODIMENTS

Figure 1:
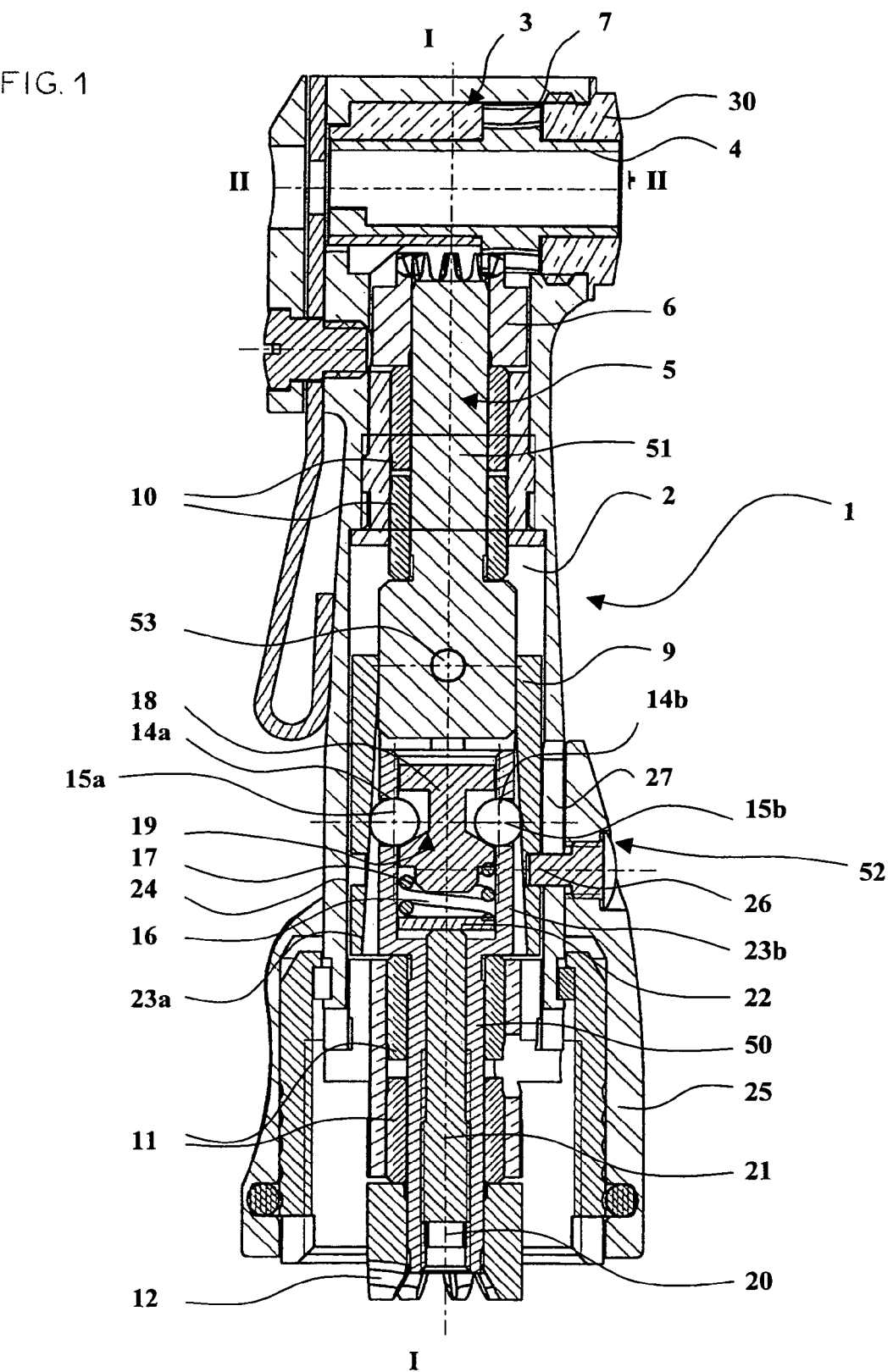
FIG. 1 is a view in longitudinal section of one embodiment of a handpiece according to the present invention.

In all the embodiments shown in the figures, a dental handpiece according to the invention includes a handpiece neck 1 in which there is a longitudinal bore 2 communicating with a transverse bore 3 of a handpiece head 30 which is fastened to it. A transverse tool-carrier shaft 4 is mounted in the transverse bore 3 of the handpiece head 30 to rotate about the transverse axis II—II, and includes a tool-holder for separably fixing a tool to the tool-carrier shaft 4.

A drive shaft 5 is mounted in the longitudinal bore 2 to rotate about the longitudinal axis I—I. The drive shaft 5 is made up of a primary shaft 50 and a secondary shaft 51 which are coaxial and coupled together in series by means 52 for limiting the maximum torque that can be transmitted. The secondary shaft 51 is guided by bearings 10, and has at its distal end, near the tool, a gear 6 which cooperates with peripheral teeth 7 on the tool-carrier shaft 4. Between the adjacent ends of the primary shaft 50 and secondary shaft 51 are the mechanical coupling means 52 for limiting the mechanical torque transmitted; these one bring about a clutch-release effect if the resisting torque applied to a tool held by the tool-carrier shaft 4 exceeds a particular torque threshold.

Figure 9:
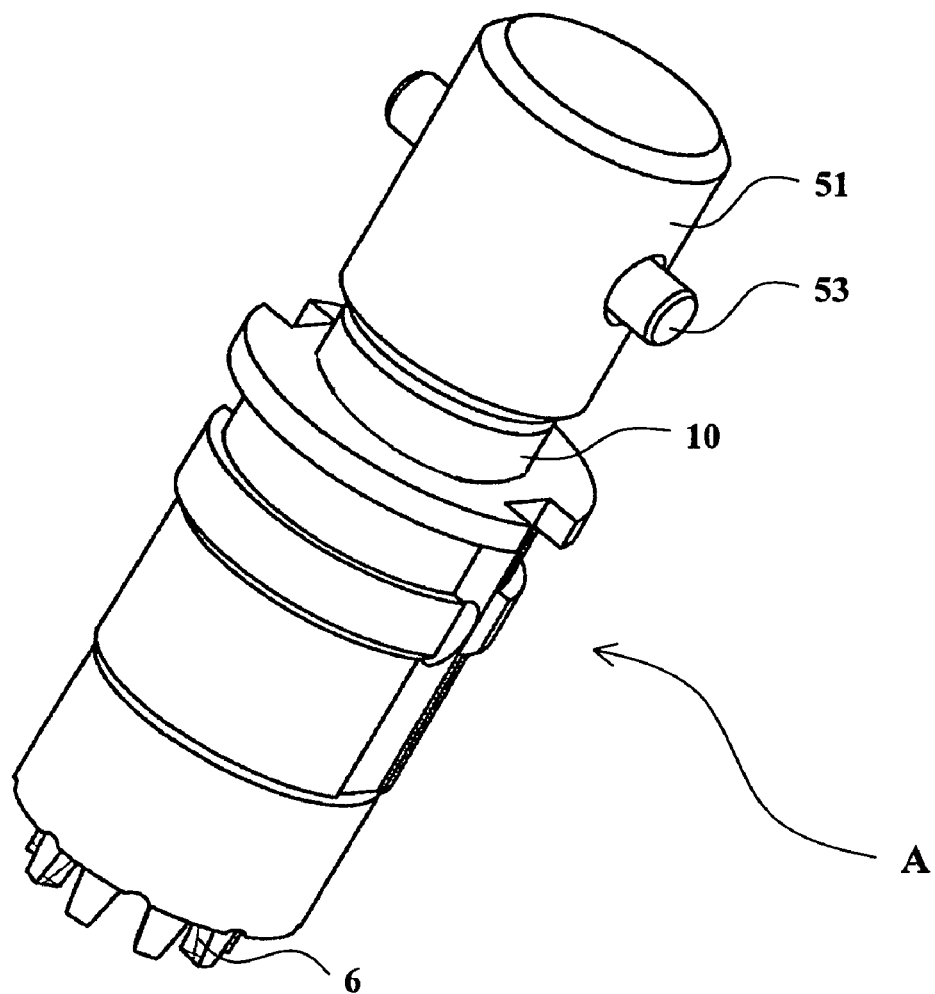
FIG. 9 is a perspective view of the driven subassembly.
Figure 10:
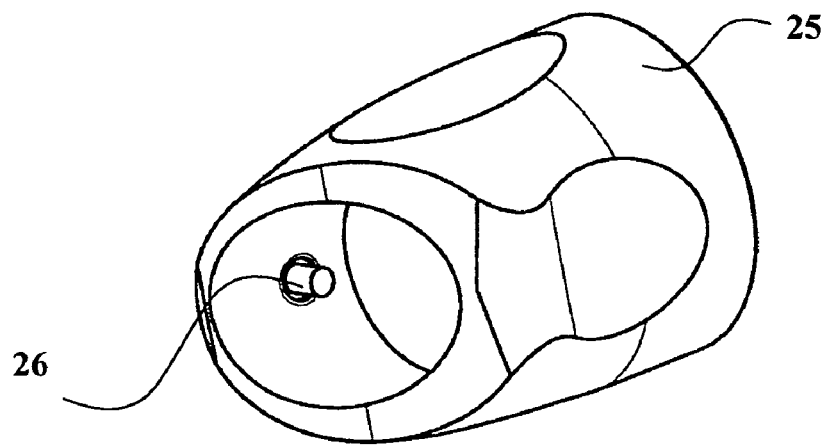
FIG. 10 is a perspective view of the adjuster ring.

In the embodiment shown in the figures, the secondary shaft 51 has at its other, proximal end projecting portions, for example the ends of a pin 53 (see FIG. 9), adapted to cooperate with slots 8a and 8b (see FIGS. 7 and 8) in a sliding coupling ring 9 for positive driving of rotation of the secondary shaft 51 by said ring 9, which is also able to slide longitudinally. This secondary shaft 51 and its guide means form a driven subassembly A shown separately in FIG. 9.

The primary shaft 50 is also mounted in the longitudinal bore 2 in bearings 11 and rotates about the longitudinal axis I—I. This primary shaft 50 has at its proximal end opposite the tool a gear 12 adapted to cooperate with a drive gear at the end of the transmission system in the main body of the handpiece, not shown in the figures. The primary shaft 50 has at its opposite, distal end two transverse passages 14a and 14b which are diametrally opposed and each of which is adapted to receive a coupling ball 15a or 15b. This transverse passages 14a and 14b can advantageously be oblique to the radial directions, as shown in FIG. 4, to provide a different clutch-release threshold according to the rotation direction. This distal end of the primary shaft 50 further includes an axial bore 16 into which the transverse passages 14a and 14b open and which is adapted to receive a compression coil spring 17 and a bearing member 18 having a frustoconical part 19 adapted to bear on the coupling balls 15a and 15b to push them radially outward in the respective transverse passages 14a and 14b. This primary shaft 50 further includes an axial bore 20 which has a screwthreaded portion and is adapted to receive a calibration screw 21 which bears on the spring 17 via a washer 22. This assembly of components forms the driving subassembly C, shown separately in FIG. 3.

A sliding coupling ring 9 that can move in translation is mounted on the secondary shaft 51 between the primary shaft 50 and the secondary shaft 51. This sliding coupling ring 9 also includes two diametrally opposed longitudinal internal grooves 23a and 23b with a circular arc-shaped cross section and a depth that varies in the longitudinal direction. These two longitudinal grooves 23a and 23b constitute coupling cavities and are adapted to cooperate with the coupling balls 15a and 15b to drive rotation of the secondary shaft 51 from the primary shaft 50. These longitudinal internal grooves 23a and 23b can advantageously be formed by boring two convergent cylindrical holes whose diameter is equal to or slightly greater than the diameter of the coupling bores 15a and 15b. These two bores are bored before the central bore of the sliding coupling ring 9. This sliding coupling ring 9 further includes an external groove 24.

Figure 2:
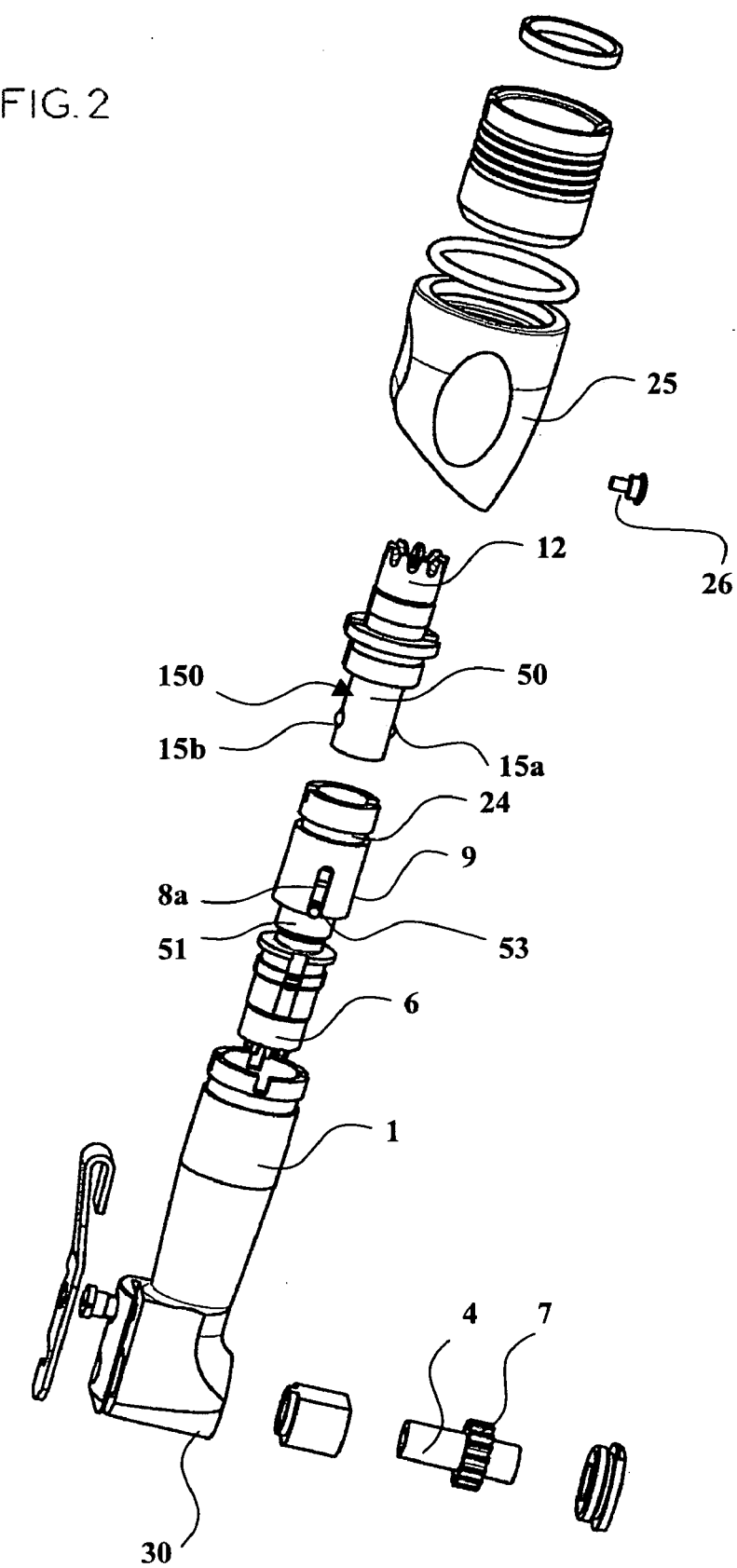
FIG. 2 is an exploded perspective view of the FIG. 1 handpiece.
Figure 3:
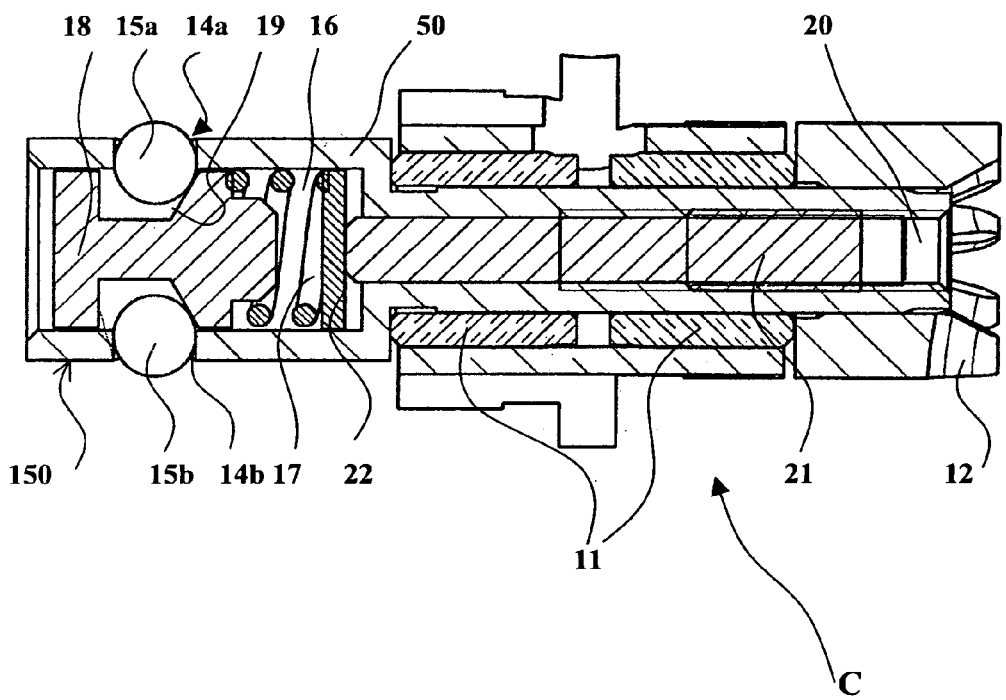
FIG. 3 is a view in longitudinal section of the driving subassembly.
Figures 4, 5:
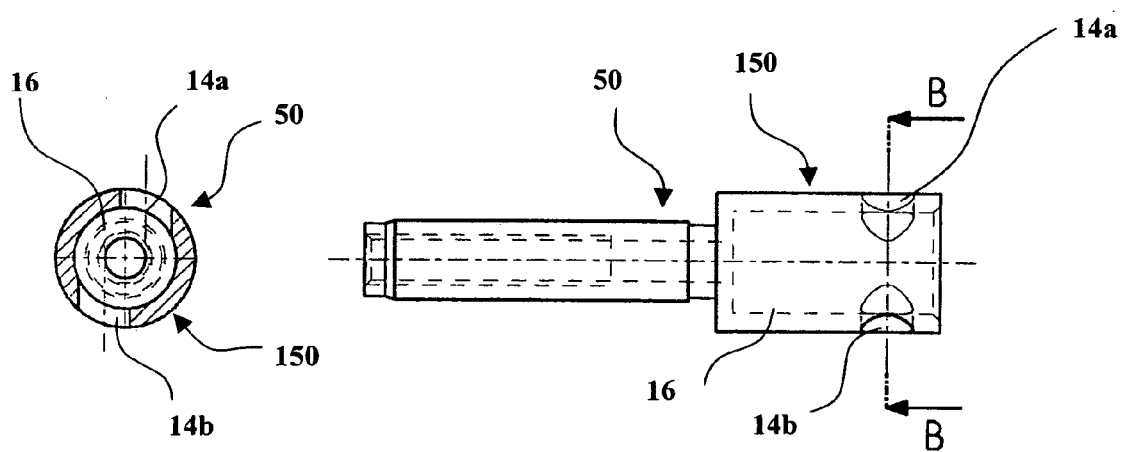
FIG. 4 is a view in section taken along the line B—B in FIG. 5.
FIG. 5 is an outside view of the primary shaft.

In the embodiment shown, the male coupling portion consists of the distal end of the primary shaft 50 with its coaxial annular outside surface 150 (see FIGS. 2 and 3). The female coupling portion consists of the coupling ring 9 constrained to rotate with the secondary shaft 51. Its coaxial annular inside surface 151 overlaps the coaxial annular outside surface 150 of the male coupling portion consisting of the primary shaft 50 (see FIGS. 6 to 8). The cavities 23a and 23b are distributed over the coaxial annular inside surface 151 of the coupling ring 9.

An adjuster ring 25 that can slide axially is mounted on the handpiece neck 1 and is directly accessible to the user. The adjuster ring 25 has an interior projection 26 that passes through a longitudinal slot 27 in the handpiece neck 1 and engages in the groove 24 to move the sliding coupling ring 9 axially, at the same time allowing it to rotate freely with the secondary shaft 51.

In use, if the resisting torque applied by the tool to the secondary shaft 51 becomes equal to or greater than the maximum permitted threshold, the coupling balls 15a, 15b are subjected to a reaction force by the internal grooves 23a, 23b of the coupling ring 9 that tends to move them closer together, against the action of the spring 17. The balls 15a, 15b can then become disengaged and exit the interior grooves 23a and 23b, allowing free rotation of the primary shaft 50 and the secondary shaft 51 relative to each other. The balls 15a and 15b then reach the other internal grooves 23b and 23a, respectively, producing a clicking sound, and can escape if the torque remains high enough. This produces a clutch-release effect that limits the torque transmitted and prevents the tool engaged in the tool-carrier shaft from breaking.

The adjuster ring 25 moves the coupling ring 9 longitudinally, which varies the threshold for the maximum torque that can be transmitted because the coupling balls 15a, 15b engage in deeper or shallower portions of the longitudinal grooves 23a and 23b. The deeper the portion of the longitudinal groove 23a and 23b, the shorter the distance the coupling ball 15a or 15b is pushed toward the axis I—I for a given drive torque, and thus the higher the maximum permitted torque value prior to clutch release that it procures.

MODE OF OPERATION

The user places the tool in the head 30 of the handpiece, which has previously been connected to the drive motor.

The user moves the adjuster ring 25 to the required longitudinal position, as a function of the type of tool, thereby adjusting the maximum torque that can be transmitted.

The user starts the drive motor in the normal direction and carries out the treatment. If the tool jamming torque becomes greater than the previously set maximum torque that can be transmitted, then the tool automatically stops turning and the user is made aware of this because of the clicking sound that corresponds to the passage of the balls 15a and 15b successively into the longitudinal internal grooves 23a and 23b of the coupling ring 9.

If the user can withdraw the tool from the area to be treated simply by pulling on it in the axial direction, the tool starts again automatically, and the user can continue the treatment.

If it is not possible to withdraw the tool, for example because it is tightly jammed, the user reverses the direction of rotation of the drive motor and can then withdraw the tool because, being driven with a higher torque in the reverse direction, the tool disengages from the root canal.

The present invention is not limited to the embodiments described explicitly, but encompasses variants and generalizations thereof within the scope of the following claims.

What is claimed is:

1. A dental handpiece for driving continuous rotation of a dental tool, said handpiece including a drive shaft mounted to rotate around a longitudinal axis in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted, the torque limiter means including:

a male coupling portion constrained to rotate with a first shaft of the pair of shafts comprising the primary shaft and secondary shaft, and having a coaxial annular outside surface, a female coupling portion constrained to rotate with a second shaft of the pair of shafts comprising the primary shaft and the secondary shaft, and having a coaxial annular inside surface overlapping the coaxial annular outside surface of the male coupling portion, a series of coupling cavities distributed annularly over a coaxial annular surface of a first coupling portion of the pair of coupling portions comprising the male and female coupling portions, wherein the coupling cavities are longitudinal grooves with a circular arc-shaped cross section and a depth varying in the longitudinal direction, at least one rotary coupling member with a rotation axis parallel to the longitudinal axis, mounted to slide radially in a respective transverse passage of a second coupling portion of the pair of coupling portions comprising the male and female coupling portions, and spring-loaded by spring means toward the coaxial annular surface of the first coupling portion of the pair of coupling portions comprising the male and female coupling portions so as to be partially engaged in said coupling cavities whilst remaining guided in said transverse passage(s), and adjusting means accessible by the user for voluntary adjustment of the maximum torque that can be transmitted, wherein relative longitudinal position adjustment means accessible to the user are provided for adjusting the relative longitudinal position of the male coupling portion in the female coupling portion, so that the rotary coupling member(s) engage(s) in deeper or shallower portions of the coupling cavities as a function of the chosen relative longitudinal position, which determines the maximum torque that can be transmitted.

2. A dental handpiece according to claim 1, wherein it includes at least two rotary coupling members mounted to slide radially in respective transverse passages regularly distributed around the longitudinal axis to balance the radial forces of the rotary coupling members between the male and female coupling portions.

3. A dental handpiece according to claim 1, wherein the rotary coupling member(s) are/is coupling balls.

4. A dental handpiece according to claim 1, wherein the rotary coupling member(s) are/is mounted to slide radially in a respective transverse passage in the male coupling portion, and the coupling cavities are distributed annularly over the coaxial annular surface of the female coupling portion.

5. A dental handpiece according to claim 1, wherein it includes means for adjusting the force of the spring means spring-loading the rotary coupling member(s).

6. A dental handpiece according to claim 1, wherein each of the respective transverse passages is oriented in a radial direction.

7. A dental handpiece according to claim 1, including a main handpiece body, a handpiece neck and a handpiece head, wherein the torque-limiter means are housed in the neck of the handpiece.

8. A dental handpiece for driving continuous rotation of a dental tool, said handpiece including a drive shaft mounted to rotate around a longitudinal axis in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted, the torque limiter means including:

a male coupling portion constrained to rotate with a first shaft of the pair of shafts comprising the primary shaft and secondary shaft, and having a coaxial annular outside surface, a female coupling portion constrained to rotate with a second shaft of the pair of shafts comprising the primary shaft and the secondary shaft, and having a coaxial annular inside surface overlapping the coaxial annular outside surface of the male coupling portion, a series of coupling cavities distributed annularly over a coaxial annular surface of a first coupling portion of the pair of coupling portions comprising the male and female coupling portions, at least one rotary coupling member with a rotation axis parallel to the longitudinal axis, mounted to slide radially in a transverse passage of a second coupling portion of the pair of coupling portions comprising the male and female coupling portions, and spring-loaded by spring means toward the coaxial annular surface of the first coupling portion of the pair of coupling portions comprising the male and female coupling portions so as to be partially engaged in said coupling cavities whilst remaining guided in said transverse passage, wherein the transverse passage(s) are/is oriented obliquely to the radial directions, and adjusting means directly accessible by the user for voluntary adjustment of the maximum torque that can be transmitted.

9. A dental handpiece according to claim 8, including a main handpiece body, a handpiece neck and a handpiece head, wherein the torque-limiter means are housed in the neck of the handpiece.

10. A dental handpiece according to claim 8, wherein the adjusting means is directly accessible to the user by manual adjustment free of the use of tools.

11. A dental handpiece for driving continuous rotation of a dental tool, said handpiece including a drive shaft mounted to rotate around a longitudinal axis in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted, the torque limiter means including:

a male coupling portion constrained to rotate with a first shaft of the pair of shafts comprising the primary shaft and secondary shaft, and having a coaxial annular outside surface, wherein the male coupling portion is constituted by the distal end of the primary shaft, a female coupling portion constrained to rotate with a second shaft of the pair of shafts comprising the primary shaft and the secondary shaft, and having a coaxial annular inside surface overlapping the coaxial annular outside surface of the male coupling portion, wherein the female coupling portion is a coupling ring mounted to overlap the adjacent ends of the primary shaft and the secondary shaft, and coupled to the secondary shaft by rotation-preventing means, a series of coupling cavities distributed annularly over a coaxial annular surface of a first coupling portion of the pair of coupling portions comprising the male and female coupling portions, at least one rotary coupling member with a rotation axis parallel to the longitudinal axis, mounted to slide radially in a transverse passage of a second coupling portion of the pair of coupling portions comprising the male and female coupling portions, and spring-loaded by spring means toward the coaxial annular surface of the first coupling portion of the pair of coupling portions comprising the male and female coupling portions so as to be partially engaged in said coupling cavities whilst remaining guided in said transverse passage, and adjusting means directly accessible by the user for voluntary adjustment of the maximum torque that can be transmitted, wherein the distal end of the primary shaft includes transverse passages for guiding coupling balls, the distal end of the primary shaft includes an axial bore into which the transverse passages open, a bearing portion is mounted to slide axially in said axial bore and has a frustoconical part in contact with the coupling balls to urge them radially outward, and a compression spring is engaged axially between the bearing portion and a calibration screw itself functionally engaged in a screwthreaded section of the axial bore.

12. A dental handpiece according to claim 11, wherein:
the handpiece has a handpiece body;
the coupling ring is slidably mounted on the proximal end of the secondary shaft, and includes coupling cavities in the form of longitudinal grooves whose depth varies in the longitudinal direction,
the coupling ring is freely rotatable and is constrained to move in axial translation with an adjuster ring itself slidably mounted on the handpiece body to be directly accessible to the user.

13. A dental handpiece according to claim 11, including a main handpiece body, a handpiece neck and a handpiece head, wherein the torque-limiter means are housed in the neck of the handpiece.

14. A dental handpiece according to claim 11, wherein the adjusting means is directly accessible to the user by manual adjustment free of the use of tools.

15. A dental handpiece for driving continuous rotation of a dental tool, said handpiece comprising:

a neck wherein balls are guided in transverse passages of an input shaft and are radially spaced apart by a support piece including a tapered part thrust by a spring; and a linking ring comprising internal longitudinal grooves with circular arc-shaped cross-section and of variable depth along the longitudinal direction, wherein said linking ring is mounted on the end of said input shaft, and mounted sliding and locked in rotation on an output shaft, wherein said balls are subjected to a reaction from said internal grooves of said linking ring under the action of a resisting torque applied by the tool to said output shaft greater than a predetermined threshold, thereby bringing said balls closer together and countering said spring, and said balls are released, producing a disengagement which limits the transmitted torque and prevents the tool from breaking.

16. A dental handpiece for driving continuous rotation of a dental tool, said handpiece comprising:

a neck wherein balls are guided in transverse passages of an input shaft and are radially spaced apart by a support piece including a tapered part thrust by a spring, said transverse passages being oriented obliquely to the radial directions; and a linking ring comprising internal longitudinal grooves with circular arc-shaped cross-section and of variable depth along the longitudinal direction, wherein said linking ring is mounted on the end of said input shaft, and mounted sliding and locked in rotation on an output shaft, wherein said balls are subjected to a reaction from said internal grooves of said linking ring under the action of a resisting torque applied by the tool to said output shaft greater than a predetermined threshold, thereby bringing said balls closer together and countering said spring, and said balls are released, producing a disengagement which limits the transmitted torque and prevents the tool from breaking.

17. A dental handpiece for driving continuous rotation of a dental tool, said handpiece including a drive shaft mounted to rotate around a longitudinal axis in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted, the torque limiter means including:

a male coupling portion constrained to rotate with a first shaft of the pair of shafts comprising the primary shaft and secondary shaft, a female coupling portion constrained to rotate with a second shaft of the pair of shafts comprising the primary shaft and the secondary shaft, a series of coupling cavities distributed annularly over a coaxial annular surface of a first coupling portion of the pair of coupling portions comprising the male and female coupling portions, at least one rotary coupling member with a rotation axis parallel to the longitudinal axis, mounted to slide radially in a transverse passage of a second coupling portion of the pair of coupling portions comprising the male and female coupling portions, and adjusting means accessible by the user for voluntary adjustment of the maximum torque that can be transmitted, wherein relative longitudinal position adjustment means accessible to the user are provided for adjusting the relative longitudinal position of the male coupling portion in the female coupling portion, so that the rotary coupling member(s) engage(s) in deeper or shallower portions of the coupling cavities as a function of the chosen relative longitudinal position, which determines the maximum torque that can be transmitted.

18. A dental handpiece for driving continuous rotation of a dental tool, said handpiece including a drive shaft mounted to rotate around a longitudinal axis in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted, the torque limiter means including:

a male coupling portion constrained to rotate with a first shaft of the pair of shafts comprising the primary shaft and secondary shaft, a female coupling portion constrained to rotate with a second shaft of the pair of shafts comprising the primary shaft and the secondary shaft, a series of coupling cavities distributed annularly over a coaxial annular surface of a first coupling portion of the pair of coupling portions comprising the male and female coupling portions, at least one rotary coupling member with a rotation axis parallel to the longitudinal axis, mounted to slide radially in a transverse passage of a second coupling portion of the pair of coupling portions comprising the male and female coupling portions, wherein the transverse passage(s) are/is oriented obliquely to the radial directions, and adjusting means directly accessible by the user for voluntary adjustment of the maximum torque that can be transmitted.

19. A dental handpiece according to claim 18, wherein the adjusting means is directly accessible to the user by manual adjustment free of the use of tools.

20. A dental handpiece for driving continuous rotation of a dental tool, said handpiece including a drive shaft mounted to rotate around a longitudinal axis in a longitudinal bore of the handpiece and made up of a primary shaft and a secondary shaft which are coaxial, coupled together in series by torque limiter means for limiting the maximum torque that can be transmitted, and provided with means for adjusting said maximum torque that can be transmitted, the torque limiter means including:

a male coupling portion constrained to rotate with a first shaft of the pair of shafts comprising the primary shaft and secondary shaft, wherein the male coupling portion is constituted by the distal end of the primary shaft, a female coupling portion constrained to rotate with a second shaft of the pair of shafts comprising the primary shaft and the secondary shaft, wherein the female coupling portion is a coupling ring mounted to overlap the adjacent ends of the primary shaft and the secondary shaft, and coupled to the secondary shaft by rotation-preventing means, a series of coupling cavities distributed annularly over a coaxial annular surface of a first coupling portion of the pair of coupling portions comprising the male and female coupling portions, at least one rotary coupling member with a rotation axis parallel to the longitudinal axis, mounted to slide radially in a transverse passage of a second coupling portion of the pair of coupling portions comprising the male and female coupling portions, and adjusting means directly accessible by the user for voluntary adjustment of the maximum torque that can be transmitted, wherein the distal end of the primary shaft includes transverse passages for guiding coupling balls, the distal end of the primary shaft includes an axial bore into which the transverse passages open, a bearing portion is mounted to slide axially in said axial bore and has a frustoconical part in contact with the coupling balls to urge them radially outward, and a compression spring is engaged axially between the bearing portion and a calibration screw itself functionally engaged in a screwthreaded section of the axial bore.

21. A dental handpiece according to claim 20, wherein the adjusting means is directly accessible to the user by manual adjustment free of the use of tools.

* * * * *